United States Patent [19]

Gitterman

[11] 3,988,463
[45] Oct. 26, 1976

[54] METHOD OF PREVENTING METASTASIS OF H. EP. NO. 3
[75] Inventor: Charles O. Gitterman, Cranford, N.J.
[73] Assignee: Merck & Co., Inc., Rahway, N.J.
[22] Filed: July 31, 1975
[21] Appl. No.: 600,553

Related U.S. Application Data
[63] Continuation-in-part of Ser. No. 467,239, May 6, 1974, abandoned.

[52] U.S. Cl. .............................................. 424/270
[51] Int. Cl.² ...................................... A61K 31/425
[58] Field of Search ................................... 424/270

[56] References Cited
OTHER PUBLICATIONS
Leiter et al., *Cancer Research*, vol. 25, part 2, No. 7, Aug. 1965, pp. 1433–1435, 1449 and 1486.

Primary Examiner—Jerome D. Goldberg
Attorney, Agent, or Firm—David L. Rose; J. Jerome Behan; Hesna J. Pfeiffer

[57] ABSTRACT 2,5-Bis-(phenyl)-thiazolo[5,4-d]thiazole of the formula:

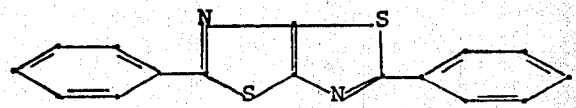

is useful in preventing in ovo metastasis of human epidermoid carcinoma.

1 Claim, No Drawings

METHOD OF PREVENTING METASTASIS OF H. EP. NO. 3

RELATIONSHIP TO OTHER APPLICATIONS

This application is a continuation-in-part of my application Ser. No. 467,239 filed May 6, 1974 which is now abandoned.

The compound, 2,5-bis-(phenyl)-thiazolo[5,4-d]thiazole, is described in the literature by J. R. Johnson et al., *J. Am. Chem. Soc.* 82, 2719 (1960). It has now been discovered that 2,5-bis-(phenyl)-thiazolo[5,4-d]thiazole inhibits metastasis of the human epidermoid carcinoma.

Metastasis can be defined as the spread of cancer cells via flowing body fluid, and the consequent establishment of new foci of growth and invasion. Transfer of the cancer is, in many cases, to an unrelated and isolated part of the body, with no observable changes in the portions of the organism between the two affected areas.

Various theories have been proposed to explain the mechanism of metastasis. Generally speaking, a tumor metastasizes from its original situs if the individual cells are less mutually adhesive. Tumor cells cannot be swept into the flowing body fluid without having first made an initial detachment from the main growth of tumor. Since tumor cells have been found within the blood stream of an affected organism without any evidence of metastasis, the spread must also depend on the tumor embolus finding a place favorable for growth within the organism.

Metastasis has a special significance within the framework of present-day cancer research. While one of the main goals of research is to find drugs which actually retard or prevent growth of the tumor at the primary site, drugs which have been discovered so far also show a similar inhibitory effect on normal cells within the treated organism. Since malignant cells proliferate extensively, the rate of inhibition of malignant cells is very high. However, epitheial lining cells of the digestive tract and bone marrow cells are normally proliferating even more rapidly, so that the advantages of using such drugs must be weighed against the harm caused to normal cells in the body.

However, with human cancer the phenomonon of metastasis still tends to dominate the entire picture of clinical prognosis and treatment. In many clinically diagnosed "hard tumors" (in which the tumor is a localized growth) surgical removal is considered the prime means of treatment. However, many times after surgery and after some delay period, the original hard tumor is observed to have metastasized so that secondary sites of cancer infection have spread throughout the patient and the patient subsequently dies of the secondary cancer growth. Metastasis is a constant occurrence in some tumors. However, many times metastasis is stimulated during the surgical operation itself. Surgery, despite modern advances, is still essentially a cutting of tissue and blood vessels and the excising of a certain portion of the patient. During the course of this operation, both normal and malignant cells are broken off tissues and pass into the blood stream of the patient. Metastasis of tumor cells during surgery is an important factor in the later development of related malignancies.

Metastasis has been studied as a function of human cancer both clinically and pathologically for many years. However, there are few experimental assays to investigate the process and mechanism of metastasis on an in vitro or laboratory scale. One reason for this is the problem of making a satisfactory study of a process that entails a whole chain of events. Another has been a difficulty experienced in elevating a study from a purely descriptive level to a quantitative plane at which level meaningful comparisons between different tumors can be made. Finally, the general use of small animals in cancer research has intended to diminish the importance in metastasis. In general, the tumors are rapidly growing localized sites which are not removed and metastasis is inconspicuous within the short term of the experiment.

The control and inhibition of metastasis is determined by experimental test procedures. One such test is described herein, and uses a human epidermoid carcinoma (H. Ep. No. 3). The description of the original tumor, the method of isolation, and the maintenance of the tumor is described in *Cancer Research* 14, p. 660–666 (1954), Toolan.

H. Ep. No. 3 is a fast growing, hemorrhagic tumor, originally obtained from the neck node of a metastatic tumor. The patient from whom the tumor was removed had had a two-year history of carefully attended leukoplakia prior to the appearance of a tumor module in the buccal mucosa. The tumor has become a useful research tool in the intervening years since the original transplant into cortisone-treated rats, primarily because it is a human cancer being propagated and maintained as a transplantable tumor in laboratory animals. H. Ep. No. 3 can be preferably maintained on the chloroioallantoic membrane of embryonated chicken eggs. In this culture, it is a heterotransplant which is not being rejected by the host but which is maintained in a state of "normal" growth within the embryonate tissue. It is also maintainable in cortisone-treated laboratory animals.

It has now been found that 2,5-bis-(phenyl)-thiazolo[5,4-d]thiazole inhibits metastasis of the human epidermoid carcinoma in an in ovo test procedure. This drug also inhibits metastasis of other tumors.

Certain chemicals have also been shown to inhibit the primary tumor growth of H. Ep. No. 3 in ovo. These compounds include cytosine arabinoside, 5-fluorouracil and 5-fluoro-2'-deoxyuridine. These compounds have been found to be active against human carcinomas in the laboratory and also clinically.

The inhibition of metastasis is determined by means of an in ovo test procedure in embryonated chicken eggs. The human epidermoid carcinoma (H. Ep. No. 3) metastasizes spontaneously from its original site of implantation on the chloroioallantoic membrane (CAM) to the chicken embryo. The extent of metastasis is estimated by removing the lung of the embryo and implanting a portion of it onto the CAM of another egg. After a suitable incubation period, H. Ep. No. 3 tumor is observed at the implantation site.

In the test procedure used, the thiazolo[5,4-d]thiazole is injected into the egg after implantation of the H. Ep. No. 3 tumor. After an incubation period of 8 days, the lung from the implanted treated egg embryo is implanted onto the CAM of normal 10 day embryonated egg. This is incubated for 8 days, and the resulting tumor (if any) is weighed and compared with controls where no thiazole compound is used. Thus, the effect of treatment by the thiazole compound on metastasis of the H. Ep. No. 3 tumor is determined.

Using this procedure, it was discovered that metastasis of the H. Ep. No. 3 tumor was inhibited without inhibiting growth of the tumor at the primary site. The lack of inhibition of tumor growth at the primary site is desirable in a procedure such as this, since it indicates that metastasis of tumor to the embryonated egg has been selectively inhibited by the drug.

This use of 2,5-bis-(phenyl)-thiazolo[5,4-d]thiazole is of importance in in ovo studies of cell metabolism, and the mechanism of metastasis of various carcinoma tumors.

The thiazolo[5,4-d]thiazole described herein also converts the H. Ep. No. 3 tumor in the embryonated egg from a hemorrhagic to a non-hemorrhagic tissue.

A sterile suspension may be formulated according to the known art using excipients suitable for the manufacture of aqueous suspensions. Such excipients are suspending agents, for example, sodium carboxymethyl cellulose, methyl cellulose, hydroxypropylmethyl cellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example, polyoxyethylene sorbitan monooleate. The sterile injectable preparation may also be a sterile injectable solution or suspension in a non-toxic parenterally acceptable diluent or solvent, for example as a solution in 1,2-butone diol.

The pharmaceutical compositions may be formulated so that for every 100 parts by weight of the composition there are present between 5 and 95 parts by weight of the active ingredient and preferably between 25 and 85 parts by weight of the active ingredient. The dosage unit form will generally contain between about 100 mg. and about 500 mg. of the active ingredient.

We claim:

1. The method for inhibiting metastasis of the H. Ep. No. 3 carcinoma in ovo which comprises treating a H. Ep. No. 3 tumor-bearing embryonated chicken egg with 2,5-bis-(phenyl)-thiazolo[5,4-d]thiazole.

* * * * *